US00PP15712P2

(12) United States Plant Patent
Kordes

(10) Patent No.: US PP15,712 P2
(45) Date of Patent: Apr. 5, 2005

(54) FLORIBUNDA ROSE PLANT NAMED 'KORSUFLABE'

(50) Latin Name: *Rosa hybrida*
Varietal Denomination: KORsuflabe

(75) Inventor: Wilhelm Kordes, Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 107 days.

(21) Appl. No.: 10/691,234

(22) Filed: Oct. 21, 2003

(51) Int. Cl.[7] ..... A01H 5/00
(52) U.S. Cl. ..... Plt./141

(58) Field of Search ..... Plt./141, 143, 145, Plt./147, 104

(56) References Cited

U.S. PATENT DOCUMENTS

PP5,001 P * 3/1983 Warriner ..... Plt./145
PP5,248 P * 6/1984 Vargas ..... Plt./111

* cited by examiner

*Primary Examiner*—Anne Marie Grunberg
*Assistant Examiner*—June Hwu
(74) *Attorney, Agent, or Firm*—Klarquist Sparkman, LLP

(57) ABSTRACT

Floribunda rose plant having large, double flowers in large clusters; disease resistance foliage; compact, well branched plant habit; and ability to grow vigorously on its own roots.

1 Drawing Sheet

Genus and species: *Rosa hybrida.*
Variety denomination: 'KORsuflabe'.

ORIGIN OF THE INVENTION

The present invention relates to a new and distinct variety of a floribunda rose plant named 'KORsuflabe' which was originated by me by crossing the variety 'TANeitber' (Bernstein-Rose) (not patented), with the variety 'JACjem' (Sunflare), U.S. Plant Pat. No. 5,001.

BACKGROUND OF THE INVENTION

The primary objective of this breeding was to produce a new rose variety having the deep gold, apricot flower color and high petal count of the female parent combined with the compact spreading habit, good clustering ability and disease resistance of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Large, double flowers in large clusters.
2. Disease resistant foliage.
3. Compact, well branched plant habit.
4. Ability to grow vigorously on its own roots.

Asexual reproduction of this new variety by cuttings, as performed at Sparrieshoop, Germany, and Wasco, Calif., shows that the foregoing and all other characteristics and distinctions come true to form and are established and transmitted through succeeding propagations.

Comparison with Parents

The subject variety differs fron the female parent in that it has much lighter flower color, larger clusters and less scent than 'TANeitber' and differs from 'JACjem' in that 'KORsuflabe' has more petals, more of an apricot flower color and more scent than 'JACjem'.

Comparison with Similar Variety

The subject variety differs with more petals, more of an apricot flower color and more scent than 'JACjem', the closest known variety.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—'TANeitber', not patented.
*Pollen parent.*—'JACjem', U.S. Pat. No. 5,001.

FLOWER

Observations made from plants commencing at two years of age grown in a garden environment at Somis, Calif.

Blooming habit: Continuous.
Bud:
*Size.*—About 25–30 mm long and 20–25 mm in diameter when the petals start to unfurl.
*Form.*—The bud form is short, pointed ovoid.

*Color.*—When sepals first divide, bud color is Yellow Group 2C. When half blown, the upper sides of the petals are Yellow Orange Group 19C; and the lower sides of the petals are Yellow Group 12D.

*Sepals.*—Color: Upper surface: Green Group 138C. Sometimes under bright sun, the upper surface will be pigmented with the color Greyed-Purple Group 185C. Lower surface: Yellow-Green Group 146C. Length: 30–35 mm. Width: 11–12 mm. Shape: Subulate. Surface texture: Upper surface: Canescent. Lower surface: Coriaceous. Margin: Ciliolate. There are three normally appendaged sepals. There are two unappendaged sepals with hairy edges.

*Receptacle.*—Color: Yellow-Green Group 146B often with Greyed-Purple Group 183B pigment in exposed areas. Shape: Funnel. Size: Medium, about 11 mm. long×16 mm. wide. Surface: Smooth.

*Peduncle.*—Length: Short, averaging about 30–45 mm. Diameter: Average 2 mm. Surface: Smooth with a few glands. Color: Yellow-Green Group 146B often with Greyed-Purple Group 183A blush. Strength: Stiff.

Bloom:

*Size.*—Medium. Average open diameter is about 8–9 cm.

*Borne.*—Several together, in flat clusters of 5 to 7 blooms.

*Stems.*—Strength: Strong. Average length is about 30–35 cm with a diameter of 6–7 mm.

*Form.*—When first open: High centered. Permanence: Flattens, outer petal edges curl slightly.

*Petalage.*—Number of petals under normal conditions: 30–35.

*Color.*—The upper sides of the petals are Yellow-Orange Group 19C. The reverse sides of the petals are Yellow Group 12D. The base of each petal has a bright yellow 5 mm×5 mm color spot of Yellow Group 12C. The major color on the upper side is Yellow-Orange Group 19C.

*Variegations.*—None.

*Discoloration.*—The general tonality at the end of the first day: Little change. At the end of the third day: Petal edges change to Yellow-Orange Group 19D. Further aging: By day six the entire petal surface is Yellow-Orange Group 19D.

*Fragrance.*—Moderate, spicy.

Petals:

*Texture.*—Thick, leathery.

*Average size.*—Length: 30 mm. Width: 30 mm.

*Shape.*—Round to deltoid.

*Surface.*—Smooth.

*Margin.*—Entire. Apex Shape: Rounded. Base Shape: Rounded.

*Form.*—Tips slightly recurved.

*Arrangement.*—Regularly arranged, shingle-like.

*Petaloids.*—Number: 5–7 Color: Yellow-Orange Group 19C.

*Persistence.*—Petals drop off cleanly before drying.

*Lastingness.*—On the plant: Fair (about 6 days). As a cut flower: Fair (about 7 days).

Reproductive parts:

*Stamens.*—Number: 70–80. Length: 8–10 mm. Anthers: Length: 2 mm. Color: Yellow-Orange Group 15C. Arrangement: Regular around styles, mixed with petaloids. Filaments: Color: Yellow Group 12A. Length: 6–8 mm. Pollen: Color: Greyed-Orange Group 167C.

*Pistils.*—Number: 60–70. Length: 7–8 mm. Styles: Color: Red Group 46C. Length: 5–6 mm. Stigmas: Color: Yellow-White Group 158A. Length: 1 mm.

*Hips.*—None observed.

PLANT

*Form.*—Bush.

*Growth.*—Vigorous, upright, branching.

*Age at maturity.*—2 years.

*Mature plant.*—Height: 100 cm. Width: 80 cm.

*Rootstock.*—Own roots.

Foliage: Number of leaflets on normal mid-stem leaves: 9 or 7, sometimes 5.

*Leaf size.*—About 150 mm. long×110 mm. wide.

*Quantity.*—Abundant.

*Color.*—New foliage: Upper side: Greyed-Red Group 178B on leaf margins, Yellow-Green Group 146D in the center of the leaf. Lower side: Greyed-Red Group 178B on leaf margins, Yellow-Green Group 146D in the center of the leaf. Old foliage: Upper side: Green Goup 139A. Lower side: Green Group 137C.

Leaflets:

*Size.*—About 50 mm long×30 mm wide.

*Shape.*—Pointed oval.

*Base shape.*—Rounded.

*Apex shape.*—Acuminate.

*Texture.*—Leathery, glossy.

*Edge.*—Serrated.

*Serrations.*—Single.

*Petiole.*—Color: Yellow-Green Group 146C.

*Petiole rachis.*—Color: Yellow-Green Group 146B. Underside: Smooth.

*Auricle shape, if present.*—None.

*Stipules.*—Length: 15–17 mm, serrated. Color: Lower surfaces Green Group 137B. Shape: Adnate.

*Disease resistance.*—Resistant to mildew, blackspot and rust under normal growing conditions.

*Pest resistance.*—Not observed.

*Vein color.*—Green Group 137A.

*Venation pattern.*—Reticulate.

Wood:

*New wood.*—Color: Yellow-Green Group 146D. Bark: Smooth.

*Old wood.*—Color: Yellow-Green Group 146A. Bark: Smooth.

Prickles:

*Quantity.*—On main canes from base: Ordinary. On laterals from main canes: Few.

*Form.*—Hooked downward.

*Length.*—4 mm.

*Color when young.*—Yellow-Green Group 146D.

*Color when mature.*—Greyed-Orange Group 176D.

Small prickles:

*Quantity.*—On main stalks: None. On laterals: None.

*Color.*—None.

Winter hardiness: Hardy to Zone 5.

I claim:

1. A new and distinct variety of rose plant of the floribunda class, substantially as herein shown and described, characterized particularly by large, double flowers in large clusters; disease resistant foliage; compact, well branched plant habit; and ability to grow vigorously on its own roots.

* * * * *

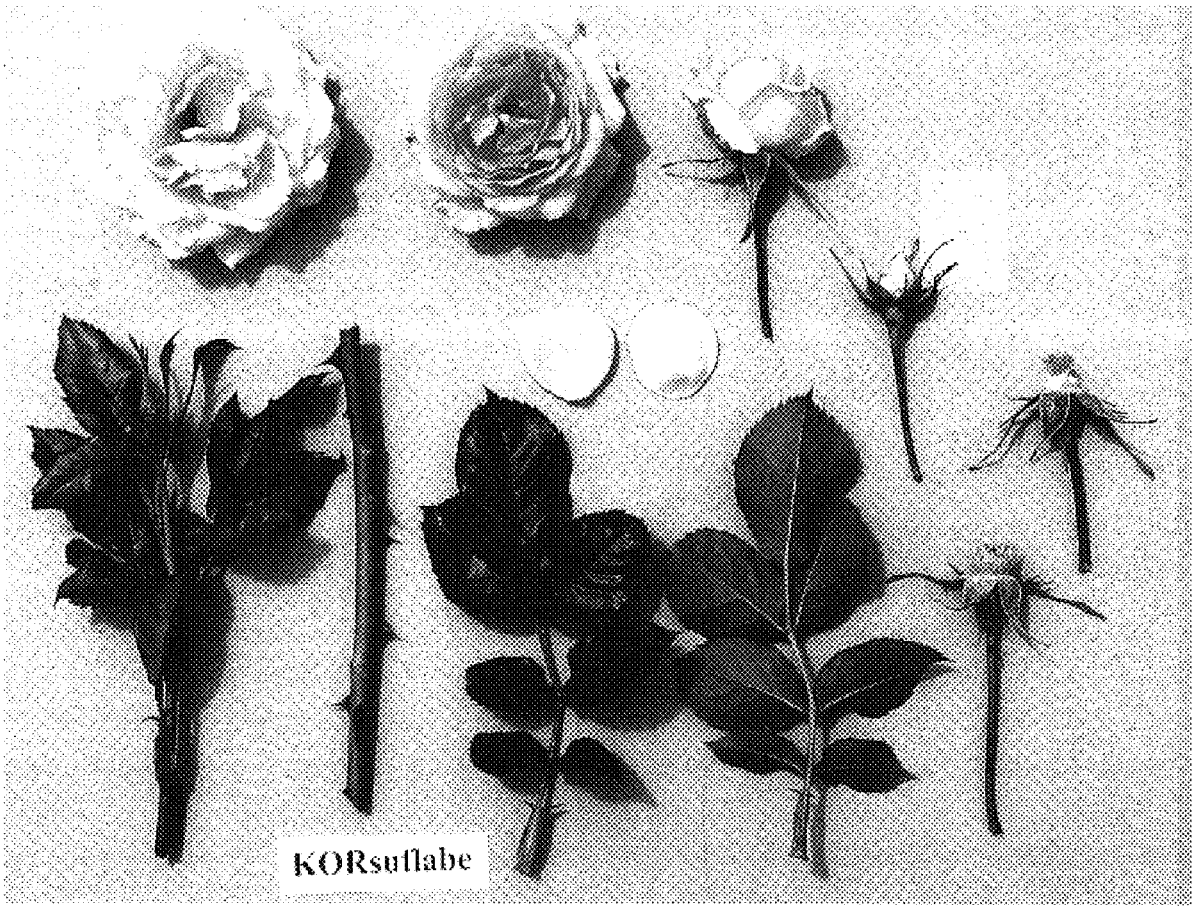
KORsuflabe